United States Patent
Adams, Jr. et al.

(10) Patent No.: US 11,212,972 B2
(45) Date of Patent: Jan. 4, 2022

(54) METHOD AND APPARATUS FOR SUBSTANTIALLY ISOLATING PLANT TISSUES

(71) Applicant: MONSANTO TECHNOLOGY LLC, St. Louis, MO (US)

(72) Inventors: Whitney R. Adams, Jr., Mystic, CT (US); Brandon Davis, North Stonington, CT (US); Lubomyr Kucher, Waterford, CT (US); Brenda A. Lowe, Mystic, CT (US); Michael Spencer, Mystic, CT (US); Michael T. Mann, Sacramento, CA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/553,911

(22) Filed: Aug. 28, 2019

(65) Prior Publication Data
US 2020/0053970 A1    Feb. 20, 2020

Related U.S. Application Data

(60) Division of application No. 15/452,519, filed on Mar. 7, 2017, now Pat. No. 10,433,503, which is a (Continued)

(51) Int. Cl.
*C12N 15/82* (2006.01)
*A01H 5/10* (2018.01)
(Continued)

(52) U.S. Cl.
CPC ............... *A01H 4/003* (2013.01); *A01G 7/00* (2013.01); *A01H 4/001* (2013.01); *A01H 4/008* (2013.01);
(Continued)

(58) Field of Classification Search
CPC . A01H 1/00; A01H 4/00; A01H 4/008; C12N 15/8201; C12N 15/82; A01G 7/00
See application file for complete search history.

(56) References Cited

U.S. PATENT DOCUMENTS

| 1,849,786 A | 3/1932 | Bloede et al. |
| 2,283,449 A | 5/1942 | Meneux et al. |

(Continued)

FOREIGN PATENT DOCUMENTS

| BR | 9917361 | 5/2011 |
| BR | P19917361-1 | 5/2011 |

(Continued)

OTHER PUBLICATIONS

Green et al.; Plant Regeneration from Tissue Cultures of Maize; Crop Science, vol. 15; pp. 417-421; 1975.*

(Continued)

*Primary Examiner* — Kent L Bell
(74) *Attorney, Agent, or Firm* — Dentons US LLP; David Lanzotti, Esq.

(57) ABSTRACT

The present invention discloses and claims methods and devices for the rapid mechanical isolation of monocot plant tissues suitable for transformation or tissue culture. The invention includes mechanical devices for substantially isolating target plant tissues for use as transformable explants, and propagation of transgenic plants and plant tissues.

12 Claims, 7 Drawing Sheets

Related U.S. Application Data continuation of application No. 14/314,963, filed on Jun. 25, 2014, now Pat. No. 9,648,814, which is a continuation of application No. 13/104,841, filed on May 10, 2011, now abandoned, which is a continuation of application No. 12/192,932, filed on Aug. 15, 2008, now Pat. No. 7,937,890, which is a division of application No. 11/054,330, filed on Feb. 9, 2005, now Pat. No. 7,560,611, which is a continuation-in-part of application No. 10/911,191, filed on Aug. 4, 2004, now Pat. No. 7,150,993.

(60) Provisional application No. 60/493,011, filed on Aug. 5, 2003.

(51) Int. Cl.
  *A01H 1/00* (2006.01)
  *A01G 7/00* (2006.01)
  *A01H 4/00* (2006.01)
(52) U.S. Cl.
  CPC ............... *A01H 5/10* (2013.01); *C12N 15/82* (2013.01); *C12N 15/8201* (2013.01); *C12N 15/8205* (2013.01)

(56) References Cited

U.S. PATENT DOCUMENTS

| | | |
|---|---|---|
| 3,104,692 A | 9/1963 | Turner |
| 3,301,292 A | 1/1967 | O'Connor |
| 3,667,523 A | 6/1972 | Lynn et al. |
| 3,744,399 A | 7/1973 | Bonteil |
| 4,066,012 A | 1/1978 | Satake et al. |
| 4,220,287 A | 9/1980 | Boczewski |
| 4,245,553 A | 1/1981 | Nakamura |
| 4,301,183 A | 11/1981 | Giguere |
| 4,326,358 A | 4/1982 | Lawrence et al. |
| 4,986,997 A | 1/1991 | Posner et al. |
| 5,004,863 A | 4/1991 | Umbeck |
| 5,015,580 A | 5/1991 | Christou et al. |
| 5,073,675 A | 12/1991 | Jones et al. |
| 5,164,310 A | 11/1992 | Smith et al. |
| 5,415,085 A | 5/1995 | Thomson |
| 5,846,797 A | 12/1998 | Strickland |
| 5,914,451 A | 6/1999 | Martinell et al. |
| 5,952,230 A | 9/1999 | Kim et al. |
| 6,384,301 B1 | 5/2002 | Martinell et al. |
| 6,537,826 B1 | 3/2003 | Horigane |
| 6,581,535 B2 | 6/2003 | Barry et al. |
| 7,057,089 B2 | 6/2006 | Ranch et al. |
| 7,067,834 B2 | 6/2006 | Horigane et al. |
| 7,150,993 B2 | 12/2006 | Davis et al. |
| 7,154,027 B2 | 12/2006 | Demmer et al. |
| 7,229,034 B2 | 6/2007 | Feazel et al. |
| 7,345,218 B1 | 3/2008 | Jiao et al. |
| 1,402,134 A1 | 7/2008 | Martinell et al. |
| 7,402,734 B2 | 7/2008 | Martinell et al. |
| 7,560,611 B2 | 7/2009 | Adams et al. |
| 7,658,033 B2 | 2/2010 | Martinell et al. |
| 7,694,457 B2 | 4/2010 | Martinell et al. |
| 7,888,552 B2 | 2/2011 | Ye et al. |
| 7,935,529 B2 | 5/2011 | Davis et al. |
| 7,937,890 B2 | 5/2011 | Adams et al. |
| 8,030,544 B2 | 10/2011 | Martinell et al. |
| 8,044,260 B2 | 10/2011 | Dersch et al. |
| 8,323,974 B2 | 12/2012 | Davis et al. |
| 8,362,317 B2 | 1/2013 | Calabotta et al. |
| 8,609,934 B2 | 12/2013 | Fillatti et al. |
| 8,937,216 B2 | 1/2015 | Dersch et al. |
| 9,006,513 B2 | 4/2015 | Calabotta et al. |
| 2002/0184663 A1 | 12/2002 | Sun et al. |
| 2003/0018995 A1 | 1/2003 | Dresselhaus et al. |
| 2003/0074686 A1 | 4/2003 | Heinz et al. |
| 2004/0034889 A1 | 2/2004 | Khan et al. |
| 2005/0042305 A1 | 2/2005 | Endo et al. |
| 2005/0044595 A1 | 2/2005 | Arias et al. |
| 2005/0158699 A1 | 7/2005 | Kadkade et al. |
| 2006/0005273 A1 | 1/2006 | Rudrabhatla et al. |
| 2006/0059589 A1 | 3/2006 | Martinell et al. |
| 2006/0260012 A1 | 11/2006 | Khan |
| 2007/0039075 A1 | 2/2007 | Tissot et al. |
| 2011/0271410 A1 | 11/2011 | Adams et al. |
| 2012/0054918 A1 | 3/2012 | Dersch et al. |
| 2018/0135063 A1 | 5/2018 | Calabotta et al. |
| 2018/0148730 A1 | 5/2018 | Dersch et al. |
| 2020/0199603 A1 | 6/2020 | Calabotta et al. |
| 2021/0254084 A1 | 8/2021 | Calabotta et al. |

FOREIGN PATENT DOCUMENTS

| | | |
|---|---|---|
| CN | 1302900 A | 7/2001 |
| CN | 1838995 A | 9/2006 |
| EP | 0298722 | 1/1989 |
| EP | 0 356 987 | 3/1990 |
| EP | 0 380 055 | 8/1990 |
| EP | 0 339 577 | 6/1993 |
| EP | 0740897 | 11/1999 |
| EP | 0958863 | 11/1999 |
| EP | 1142489 | 10/2001 |
| EP | 1 236 801 | 9/2002 |
| GB | 402848 | 6/1933 |
| GB | 439399 | 12/1935 |
| GB | 657644 | 9/1951 |
| GB | 861711 | 3/1958 |
| GB | 1459551 | 12/1976 |
| JP | 59-082063 | 5/1984 |
| JP | 10-276748 | 10/1998 |
| JP | 11-164678 | 6/1999 |
| JP | 2001-17107 | 1/2001 |
| JP | 292717 | 10/2001 |
| JP | 2002-119886 A | 4/2002 |
| JP | 2003-339395 | 12/2003 |
| JP | 2004-357547 | 12/2004 |
| WO | WO 1992/15675 | 9/1992 |
| WO | WO 1995/06722 | 9/1995 |
| WO | WO 1996/10341 | 4/1996 |
| WO | WO 1998/01575 | 1/1998 |
| WO | WO 1999/02267 | 1/1999 |
| WO | WO 1999/10513 | 3/1999 |
| WO | WO 1999/20776 | 4/1999 |
| WO | WO 2000/42207 | 7/2000 |
| WO | WO 2000/77230 | 12/2000 |
| WO | WO 2000/077230 | 12/2000 |
| WO | WO 2001/29241 | 4/2001 |
| WO | WO 2002/00010 | 1/2002 |
| WO | WO 2002/37987 | 5/2002 |
| WO | WO 2002/066599 | 8/2002 |
| WO | WO 2003/017752 | 3/2003 |
| WO | WO 2003/100381 | 12/2003 |
| WO | WO 2004/000006 | 12/2003 |
| WO | WO 2004/006667 | 1/2004 |
| WO | WO 2005/000471 | 1/2005 |
| WO | WO 2005/122750 | 12/2005 |
| WO | WO 2006/026466 | 3/2006 |
| WO | WO 2007/079538 | 7/2007 |
| WO | WO 2007/103769 | 9/2007 |

OTHER PUBLICATIONS

Kumlehn et al.; In vitro development of wheat (*Triticum aestivum* L.) from zygote to plant via ovule culture; Plant Cell Reports 16: 663-667; 1997.*
U.S. Appl. No. 16/723,853, filed Dec. 20, 2019, Calabotta et al.
U.S. Appl. No. 16/904,347, filed Jun. 17, 2020, Dersch et al.
U.S. Appl. No. 17/124,115, filed Dec. 16, 2020, Calabotta, et al.
Abdelnour-Esquivel et al., "Cryopreservation of Zygotic Embryos of *Coffea* ssp.," Cryo-Letters 13:297-302, 1992.
Baker et al., "High frequency somatic embryogenesis in peanut (*Arachis hypogaea* L.) using mature, dry seed," *Plant Cell Reports* 15:38-42, 1995.
Barros et al., "Transformação Genética De *Coffea arabica* Através De Bombardeamento," *Biotecnologia* pp. 150-152, 2000.

(56) References Cited

OTHER PUBLICATIONS

Engelmann, "Plant Cryopreservation: Progress and Prospects," In Vitro Cell. Dev. Biol.—Plant 40:427-433, 2004.
Green et al., "Plant Regeneration from Tissue Cultures of Maize," *Crop Science* 15:417-721, 1975.
Hewezi et al., "Dehydrating Immature Embryo Split Apices and Rehydrating with *Agrobacterium tumefaciens*: A New Method for Genetically Transforming Recalcitrant Sunflower," *Plant Mol. Bio. Rep.* 20:335-345. 2002.
Higley et al., "Effects of non-destructive tissue extraction on the viability of corn, soybean, and bean seeds", *Seed Science and Technology*, 22(2):245-252, 1994.
Kameswara, "Plant genetic resources: Advancing conservation and use through biotechnology," *African J of Biotech*: vol. 3(2), pp. 136-145, Feb. 2004.
Kunlehn et al., "In vitro development of wheat (*Tritcum aestivum* L.) from zygote to plant via ovule culture," *Plant Cell Reports* 16:663-667; 1997.
Lacorte et al., "Transient expression of GUS and the 2S albumin gene from Brazil nut in peanut (*Arachis hypogaea* L.) seed explants using particle bombardment," *Plant Cell Reports* 16:619-623, 1997.
Matthys-Rochon, "In vitro development of maize immature embryos: a tool for embryogenesis analysis," *Journal of Experimental Botany* 49(322):839-845, 1998.
Moon et al., "Effects of Proliferation, Maturation, and Desiccation Methods on Conversion of Soybean Somatic Embryos," In Vitro Cell. Dev. Biol.—Plant 39:623-628, 2008.
Orlikowska, "Effect of in vitro storage at 4° C. on survival and proliferation of two apple rootstocks," *Plant Cell. Tissue and Organ Culture* 31:1-7, 1992.
Patnaik et al., "*Agrobacterium*-mediated transformation of mature embryos of *Triticum aestivum* and *Triticum durum*," *Current Science* 91:307-317, 2006.
Paz et al., "Improved cotyledonary node method using an alternative explant derived from mature seed for efficient agrobacterium-mediated soybean transformation," Plant Cell Rep., 25:206-213, 2006.

Popelka et al., "Genetic transformation of cowpea (*Vigna unguiculata* L.) and stable transmission of the transgenes to progeny," *Plant Cell Rep.* 25:304-312, 2006.
Shields et al., "Use of fungicides in plant tissue culture," *Plant Cell Reports* 3:33-36, 1984.
Wang et al., "Maize (*Zea mays*) genetic transformation by co-cultivating germinating seeds with *Agrobacterium tumefaciens*," *Biotechnol. Appl. Biochem.* 46:51-55, 2007.
USPTO; Non-final Office Action for U.S. Appl. No. 13/098,781, dated Apr. 4, 2012.
USPTO; Notice of Allowability regarding U.S. Appl. No. 10/911,191, dated May 17, 2006.
USPTO; Notice of Allowance for U.S. Appl. No. 13/098,781,dated Aug. 10, 2012.
USPTO; Notice of Non-Compliant Amendment regarding U.S. Appl. No. 10/911,191 dated Jun. 3, 2005.
Office action dated Mar. 9, 2012, in European Patent Application No. 08731808.5.
Office Action issued in European Application No. 11191760.5 dated Apr. 30, 2014.
USPTO; Office Action regarding U.S. Appl. No. 10/911,191, dated Apr. 22, 2005.
USPTO; Office Action regarding U.S. Appl. No. 10/911,191, dated Sep. 12, 2005.
Office Action regarding Brazilian Application No. PI0808716-4, dated Feb. 9, 2017.
Response to Notice of Non-Compliant Amendment regarding U.S. Appl. No. 10/911,191 dated Jun. 17, 2005.
Response to Office Action regarding U.S. Appl. No. 10/911,191 dated May 20, 2005.
Response to Office Action regarding U.S. Appl. No. 10/911,191 dated Mar. 14, 2006.
Terminal Disclaimers and Response to Office Action dated Apr. 4, 2012 for U.S. Appl. No. 13/098,781,dated Jun. 29, 2012.

\* cited by examiner

METHOD AND APPARATUS FOR SUBSTANTIALLY ISOLATING PLANT TISSUES This application is a divisional of U.S. Ser. No. 15/452,519, filed Mar. 7, 2017, which is a continuation of U.S. Ser. No. 14/314,963, filed Jun. 25, 2014, now U.S. Pat. No. 9,648,814, which is a continuation of U.S. Ser. No. 13/104,841, filed May 10, 2011, now abandoned, which is a continuation of U.S. Ser. No. 12/192,932, filed Aug. 15, 2008, now U.S. Pat. No. 7,937,890, which is a divisional of U.S. Ser. No. 11/054,330, filed Feb. 9, 2005, now U.S. Pat. No. 7,560,611, which is a continuation-in-part of U.S. application Ser. No. 10/911,191, filed Aug. 4, 2004, now U.S. Pat. No. 7,150,993, which claims the benefit of priority of U.S. Provisional Application No. 60/493,011, filed Aug. 5, 2003, all of which are herein incorporated by reference in their entireties.

FIELD OF THE INVENTION

The present invention relates generally to plant propagation and mechanical methods for substantially isolating target plant tissues, such as embryos, which are suitable for genetic transformation or tissue culture.

BACKGROUND OF THE INVENTION

The preparation of tissues for plant propagation, regeneration and transformation is time consuming and labor intensive, especially as it usually involves manual excision of transformable or culturable plant tissues. For example, in corn (*Zea mays*), individual immature embryos are typically removed manually to provide genetically-transformable explants. The manual excision of embryogenic tissues is laborious and risks ergonomic injury to the worker. Moreover, when larger amounts of transformable plant tissue are required for high-throughput transformation and plant production, more workers must be employed and trained to meet the increased demands. Additionally, there can be significant variability in the quality of plant tissues obtained, depending on the skill level, care, attentiveness, and fatigue of the individual workers. This tissue variability is problematic, as poor quality tissues negatively impact the efficiency of subsequent tissue culture, genetic transformation, and plant propagation. Thus, there is a need in the art for methods of preparing target plant tissues that are more rapid, reduce the overall ergonomic burden on workers, reduce the amount of workers needed to process the plant materials, and/or yield plant tissues that are of higher quality or more consistent quality than manually produced tissues.

SUMMARY OF THE INVENTION

The present invention discloses methods and apparatuses to simplify, improve safety, increase reliability, reduce ergonomic injury, reduce the number of personnel required, and/or increase the speed with which target plant tissues are substantially isolated for use in plant tissue culture and genetic transformation. In particular, the present invention discloses and claims methods and apparatuses useful for substantially isolating embryos. In some embodiments, the methods and devices may be used to substantially isolate monocot embryos, such as corn embryos. The substantially isolated embryos are preferably suitable for genetic transformation or tissue culture. The methods and apparatuses disclosed herein are particularly useful for high-throughput processing (i.e., substantially isolating large numbers of target tissues and/or processing large quantities of seeds).

One aspect of this invention includes methods for substantially isolating target tissues from monocots, such as embryos, that are suitable for genetic transformation or tissue culture. The method comprises (a) providing monocot seeds containing immature embryos that have an opening in the pericarp or seed coat of the seeds; and (b) applying force to the seeds sufficient to substantially isolate the immature embryos from the seeds. In some embodiments, immature corn embryos are substantially isolated from corn seeds. The immature embryos thus obtained are preferably suitable for genetic transformation or tissue culture.

Another aspect of this invention provides an apparatus for substantially isolating target plant tissues, such as embryos, suitable for genetic transformation or tissue culture. The device comprises at least one aperture for guiding a fluid stream. In one embodiment, the fluid stream contacts kernels on an ear of corn and causes the embryos to become substantially isolated from the kernels. The substantially isolated embryos are preferably suitable for genetic transformation or tissue culture.

In one embodiment, the apparatus comprises at least one component selected from among (a) at least one solid surface suitable for applying mechanical positive pressure to the exterior of a seed; (b) at least one aperture for guiding a fluid flow; (c) at least one aperture for applying negative fluid pressure; and any combinations thereof. The component may be used to direct a physical force on the seed sufficient to substantially isolate a target tissue, such as an embryo. Accordingly, the apparatus may be used to substantially isolate corn embryos suitable for genetic transformation or tissue culture from an ear of corn. In some embodiments, the aperture for guiding a fluid flow directs the fluid flow to contact corn seeds or kernels on an ear of corn. In some embodiments, the aperture for applying negative fluid pressure directs the negative fluid pressure to contact corn seeds or kernels on an ear of corn. The target tissues substantially isolated by such an apparatus are preferably suitable for tissue culture or genetic transformation.

The invention further provides transgenic plants, plant tissues, and seeds. Transgenic plant and plant tissues may be produced by (a) substantially isolating a target tissue using the methods and/or apparatuses described herein, (b) introducing a heterologous nucleic acid molecule into the target tissue to produce a transformed explant, and (c) culturing the transformed explant under suitable growth conditions to produce a transgenic plant tissue or plant. Any method of transformation is suitable and known to those of skill in the art. Additionally, suitable culture and regeneration conditions are known and routine. The transgenic plant, plant tissue, or seed is preferably a monocot, such as corn. The invention also includes all progeny plants, plant tissues, and seeds that are produced from the transgenic plant tissue or plant.

Other embodiments of the invention are disclosed in the following detailed description.

BRIEF DESCRIPTION OF THE DRAWINGS

FIG. 5 (top) depicts a cross-sectional view of one embodiment of such a device, showing how the nozzle, optional suction head, and corn ear may be positioned relative to each other. FIG. 5 (bottom) schematically depicts a corn ear positioned in the device. Legend: (A) base, (B) holder, (C) nozzle, (D) suction head, (E) corn ear, and (F) aperture for guiding fluid flow.

FIG. 7 depicts

DETAILED DESCRIPTION OF THE INVENTION

Figure 1:
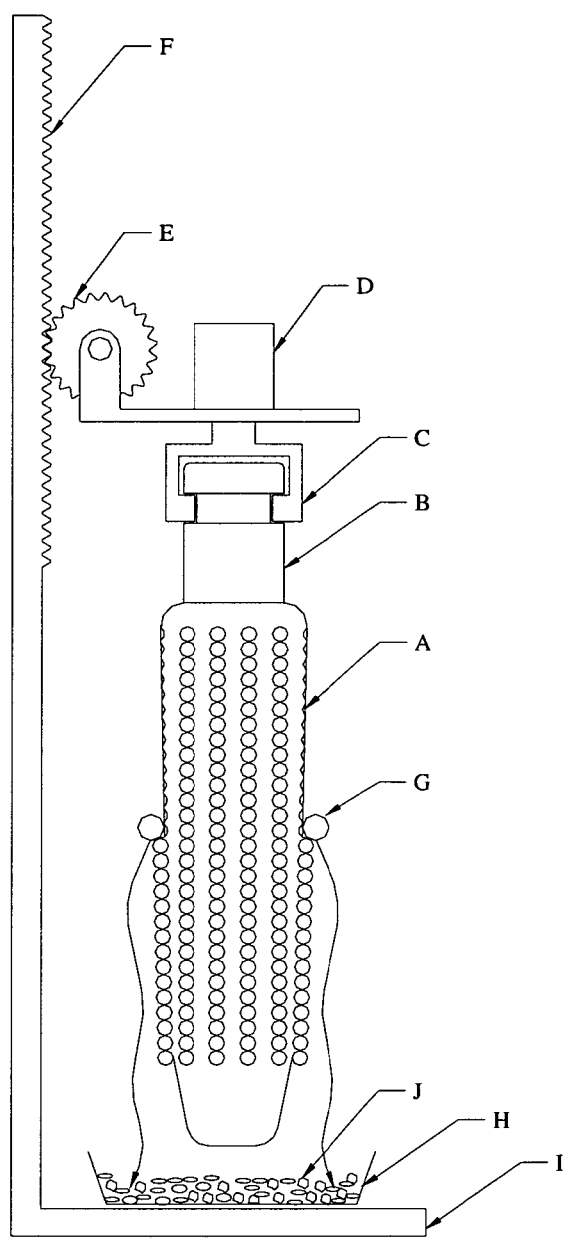
FIG. 1 depicts one embodiment of an apparatus of the present invention that uses positive mechanical pressure for substantially isolating embryos, as described in Example 4.

Unless defined otherwise, all technical and scientific terms used herein have the same meaning as commonly understood by one of ordinary skill in the art to which this invention belongs, when taken in context of the present specification. Where there are inconsistencies between the text of the specification and the material incorporated by reference, the definitions and meanings provided in the present specification are intended. The nomenclature used herein and the manufacture or laboratory procedures described below are well known and commonly employed by those of skill in the art.

The phrases "substantially isolated" or "extracted" refer to the processing of a target tissue (e.g., an embryo or other tissue explant) that resides in or forms part of a larger tissue complex (e.g., a seed) such that the target tissue is physically separated from at least half of the larger complex. In some embodiments, a substantially isolated target tissue may be physically separated from at least about 50%, 60%, 70%, 85%, 90%, 95%, 96%, 97%, 98% r 99% of the larger complex, or any fraction thereof. In other embodiments, the target tissue is physically separated from more than about 80% to about 100%, about 90% to about 100%, or about 99% to about 100% of the larger complex, or any fraction in between. In some embodiments, the target tissue may be physically separated from about 100% of the larger complex.

While a substantially isolated target tissue is physically separated from some percentage of the larger complex, it does not necessarily have to be purified from that complex. In other words, the substantially isolated target tissue may remain in a batch with the larger tissue complex, so long as the target tissue is physically separated from the complex (as described above). In some embodiments, however, it may be desirable to remove some or all of the separated complex from the substantially isolated target tissue. All such embodiments are within the scope of the present invention.

The phrase "target plant tissue" refers to a portion of a plant tissue or seed that one seeks to substantially isolate. In the present invention, target plant tissue refers to any portions of a plant or plant seed that can be substantially isolated and used for genetic transformation or tissue culture. In some embodiments, the target plant tissue is an embryo, in particular, an immature embryo from a monocot such as corn.

The phrase "suitable for genetic transformation" and "suitable for tissue culture" refer to plant tissues that are competent for transformation or growth in under suitable plant culture conditions, respectively. One of skill in the art can readily determine if a particular target tissue is suitable for genetic transformation or tissue culture by using routine experimentation. For example, a sample from a batch of substantially isolated target tissues may be cultured on a suitable plant media (also known to those of skill in the art) to determine if the tissues are capable of growth and regeneration. Similarly, samples of substantially isolated target tissues can be subject to transformation and screened for the presence of a heterologous nucleic acid molecule. Such techniques are routine and can rapidly identify which tissues are competent for transformation or tissue culture and which, if any, are not.

Where a term is provided in the singular, the inventors also contemplate aspects of the invention described by the plural of that term.

Methods for Substantially Isolating Target Plant Tissues

The present invention provides methods of substantially isolating target plant tissues suitable for genetic transformation or tissue culture, comprising (a) providing seeds containing an opening in the pericarp or seed coat of the seeds; and (b) applying force to the seeds sufficient to substantially isolate a target plant tissue from the seeds. In some embodiments, the target plant tissue is an embryo. The embryos are preferably monocot embryos, such as from corn. In some embodiments, the substantially isolated target tissue may be isolated in whole are in part. For example, a batch of substantially isolated immature embryos may include intact embryos, partial embryos, or mixtures thereof. Preferably, the intact and/or partial tissues are suitable for genetic transformation, tissue propagation, plant regeneration and other tissue culture applications.

Suitable procedures for plant tissue culture and regeneration are well known in the art. See, for example, U.S. Pat. No. 5,550,318 to Adams et al., U.S. Pat. No. 5,780,708 to Lundquist et al., United States Patent Application Publication Number 2004/0210958 to Duncan et al., United States Patent Application Publication Number 2004/0016030 to Lowe et al., and United States Patent Application Publication Number 2004/0244075 to Cai et al., which disclose transformation methods useful with corn, and United States Patent Application Publication Number 2003/0024014 to Cheng et al., which disclose transformation methods useful with wheat, all of which are incorporated by reference in their entirety herein. These tissue culture applications can include at least one process selected from transformation, callus formation, direct embryogenesis, formation of differentiated plant tissue, formation of at least one mature plant, formation of at least one fertile mature plant, and combinations of these processes. The plants regenerated from the extracted immature embryos may be regenerated, for example, through differentiation of dedifferentiated tissue (calli) or by direct embryogenesis of the extracted immature embryos. Regenerated plants can preferably be grown to maturity to provide mature plants, and more preferably fertile mature plants. The extracted immature embryos and extracted non-embryo tissues may also be used for other purposes, such as, but not limited to, genetic or biochemical analysis.

The methods and apparatuses of the present invention can be applied to any monocot plants of interest. Preferred monocots include, but are not limited to, members of the family Poaceae, including grasses such as turf grasses and grain crops such as corn (maize), wheat, and rice. Particularly preferred monocots include Zea species, including corn (Zea mays), which has multiple kernels (seeds) typically held in rows on a corn ear.

In general, the monocot seeds from which the target tissues are substantially isolated are provided in any suitable manner. For example, seeds may be attached to the ear or head on which the seeds grow; in some embodiments the monocot seeds may be removed from the ear or head prior to substantially purifying the target tissue.

In some embodiments, an opening in the pericarp or seed coat of the monocot seeds is provided. This may be accomplished by any suitable technique, such as, but not limited to, making a hole, puncture, or incision with a needle, awl, blade, or other suitable implement. In some applications of the method, no pericarp tissue need be removed; in other embodiments, the opening of the pericarp may include removal of at least part of the pericarp and possibly of some non-embryo tissue (e.g., endosperm). Preferably, the opening is sufficient to substantially separate the embryo from the seed. In some embodiments it may be necessary only to weaken the pericarp sufficiently (for example, by abrasion, or by other physical, chemical, or enzymatic treatment) so that application of force to the seed results in substantial isolation of the target tissue, such as the embryo.

The method includes the step of applying force to the seeds sufficient to substantially isolate the target tissue, such as an immature embryo, from the seeds, wherein the substantially isolated target tissue is suitable for genetic transformation and tissue culture. Force may be applied to multiple seeds consecutively or simultaneously. The applied force can be continuous or non-continuous (for example, pulsed or wave-like force), and is generally mechanically applied, that is to say, the force is obtained through the use of a device or machine rather by human hand. The amount of force applied is preferably sufficient to overcome the adhesion of the target (e.g., embryo) and non-target (e.g., non-embryo tissue such as endosperm) from each other, thus allowing separation of the target and non-target tissues. Any suitable force or forces may be employed for removal of the target tissue from its seed, and multiple forces may be used in combination, sequentially or simultaneously. Suitable forces include, but are not limited to, fluid jet positive pressure, liquid jet positive pressure, mechanical positive pressure, negative pressure, centrifugal force, linear acceleration, linear deceleration, fluid shear, fluid turbulent flow, and fluid laminar flow. Fluid forces can be exerted by any fluid, gases or liquids or combinations of both.

The method can further include the step of separating the substantially isolated target tissue, such as immature embryos, from associated non-embryo tissue such as endosperm, glumes, and seed coat or pericarp tissues. Separation may be accomplished by one or more suitable techniques, including, but not limited to, separation by size exclusion (for example, by filtration in one or more filtering steps), separation based on hydrophobicity, hydrophilicity, lipophilicity, or other attractive forces, and separation by mass or density differentials (for example, separation by centrifugation, settling, and decanting). The separation step or steps can be optional, for example, where no additional isolation of intact or partial embryos is necessary for their use in tissue culture.

The method of the invention is particularly suitable to applications where a large number of target tissues must be provided, for example, in high-throughput processes or screening, or in batch processing for genetic transformation or tissue culture. Automation of the method is possible, for example, by employing robotic or mechanical handling of the corn ears or seeds, opening of the pericarp, application of force to the seed, or the optional separation steps. Such automation may use optical or mechanical sensors to aid in positioning the corn ears or seeds relative to the applied force or forces, or in the separation steps. In one preferred embodiment, the method provides substantially isolated embryos at a rate of between about 250 to 100,000 or more embryos per employee-day; or between about 250 to about 100,000, or about 250 to about 50,000, or about 250 to about 20,000, or about 250 to about 10,000, or about 250 to about 5000, or about 250 to about 3000, or about 250 to about 1000 embryos per employee-day; or between about 800 to about 100,000, or about 800 to about 50,000, or about 800 to about 20,000, or about 800 to about 10,000, or about 800 to about 5000, or about 800 to about 3000, or about 800 to about 1000 embryos per employee-day; or between about 2500 and about 100,000, or about 2500 to about 50,000, or about 2500 to about 20,000, or about 2500 to about 10,000, or about 2500 to about 5000, or about 2500 to about 3000 embryos per employee-day; or between about 5000 and about 100,000, or about 5000 to about 50,000, or about 5000 to about 20,000, or about 5000 to about 10,000 embryos per employee-day, or any fraction or whole number in between any of the aforementioned ranges. As a reference, an employee-day is equivalent to one day's labor of one employee of average skill in the art. While average employee output can vary, the following is given as a guideline for purposes of comparing the present invention with the current average employee output. To manage the ergonomic burden, it is currently suggested that workers excise about one ear of corn per a day (approximately 200 to 300 embryos) about twice per week. Thus, an average employee following such recommendations can produce up to about 600 embryos per week. It is possible that an average employee could produce up to about 500-800 excised embryos in one day. However, maintaining such an output over the course of several days or even weeks is not recommended due to the increased ergonomic burdens and quality concerns. As noted above, the present invention overcomes these significant output limitations.

Apparatuses for Substantially Isolating Target Plant Tissues

The present invention also provides apparatuses for substantially isolating target tissues, such as corn embryos, that are suitable for genetic transformation or tissue culture. In an embodiment for separating corn embryos, such an apparatus comprises at least one aperture for guiding a fluid stream, wherein the fluid stream contacts kernels on the corn ear and substantially isolates embryos from the kernels. Generally, it is preferred that the fluid stream contact as many of the kernels in a given period of time as is convenient, so as to more rapidly isolate embryos. The at least one aperture can include a single aperture or multiple apertures (for example, single or multiple nozzles, which can include flat, round, oval, fan-shaped or other patterned nozzles, and adjustable, moving, or stationary nozzles), and can generate a fluid flow of any suitable type and medium. Fluids may be gases (such as air, nitrogen, or gas mixtures), liquids (such as water, physiological saline, or various culture media), or combinations. Suitable fluid flows include, but are not limited to, fluid jets (such as single or multiple columnar jets; flat, cone-shaped, or fan-shaped jets or sprays; and sheet-like jets), laminar fluid flow, and turbulent fluid flow. Suitable fluid flows can result in a variety of forces to remove the embryo from its kernel, including positive pressure or negative pressure or both; such forces can be uniform or non-uniform, continuous or non-continuous (such as a pulsed or wave-like force), or in any combination thereof.

The apparatus of the invention may further include a means for moving the target tissue being substantially purified and the fluid stream, relative to each other. For example, either the ear of corn containing seeds or the fluid stream, or both, may be moved. Various embodiments of the apparatus can be used with single or multiple, intact or partial ears of corn. For example, the corn ear or ears can be secured to a holder or grasper, which is moved relative to the fluid stream. In other embodiments, however, the corn ear or ears need not be individually secured to a holder but can be freely movable so as to allow multiple kernels to be contacted by the force used to remove the embryos from the kernels. The means for moving at least one corn ear relative to the fluid stream can rotate the at least one corn ear and the at least one aperture relative to each other, or can move the fluid stream along the longitudinal axis of the at least one corn ear, or can provide any suitable three-dimensional movement of the at least one corn ear and the at least one aperture relative to each other, such as a combination of rotation and longitudinal motion.

The apparatus of the invention can further include at least one separator for separating target tissues from non-target tissues. For example, embryos may be separated from non-embryo tissues, wherein the separated embryos comprise at least some corn embryos suitable for genetic transformation or tissue culture. Separators can work by any suitable mechanism, including, but not limited to, separation by size exclusion (for example, using a mesh, screen, perforated surface, or other device capable of excluding objects of a certain size), separation based on hydrophobicity or other attractive forces (for example, using a material, solid or fluid, that can attract or repel the embryos), and separation by mass or density differentials (for example, using a centrifuge, or using solutions for differential settling). In certain embodiments, the at least one separator can be optional, for example, where no additional isolation of intact or partial embryos is necessary for their use in genetic transformation or tissue culture.

The substantially isolated (and optionally separated) immature embryos include at least some embryos, such as immature intact or partial embryos, suitable for tissue culture applications, transformation, callus formation, direct embryogenesis, formation of differentiated plant tissue, formation of at least one mature plant, formation of at least one fertile mature plant, and combinations of these processes, as described above. The substantially isolated immature embryos and non-embryo tissues may also be used for other purposes, such as, but not limited to, genetic or biochemical analysis.

The present invention further provides an apparatus for mechanically substantially isolating multiple corn embryos suitable for genetic transformation or tissue culture from at least one immature corn ear, including at least one component selected from (a) at least one solid surface for applying mechanical positive pressure to the exterior of kernels on the at least one immature corn ear; (b) at least one aperture for guiding a fluid flow, wherein the fluid flow contacts kernels on the at least one immature corn ear; and (c) at least one aperture for applying negative fluid pressure, wherein the negative fluid pressure contacts kernels on the at least one immature corn ear; and wherein the at least one component applies force to the kernels sufficient to substantially isolate embryos from the kernels, the substantially isolated embryos including multiple immature embryos suitable for genetic transformation or tissue culture. A suitable apparatus applies one or more forces sufficient to substantially isolate the immature embryos from the seeds, wherein the substantially isolated immature embryos include embryos suitable for genetic transformation or tissue culture. The one or more forces may be applied to multiple seeds consecutively or simultaneously, in a continuous or non-continuous manner, and is generally applied mechanically and not manually. Multiple forces may be used in combination, sequentially, or simultaneously. Suitable forces include, but are not limited to, fluid jet positive pressure, liquid jet positive pressure, mechanical positive pressure, negative pressure, centrifugal force, linear acceleration, linear deceleration, fluid shear, fluid turbulent flow, and fluid laminar flow. Fluid forces can be exerted by any fluid, gases or liquids or combinations of both.

Combination apparatuses of the invention can optionally include a means for moving the at least one corn ear relative to the source or sources of force (that is to say, the solid surface for applying mechanical positive pressure, the aperture for guiding a fluid flow, or the aperture for applying negative fluid pressure). Preferably the ear or ears is moved relative to the source of force so that the force or forces contact as many of the kernels in a given period of time as is convenient, so as to more rapidly isolate embryos.

Combination apparatuses of the invention can further include at least one means for further separation of the substantially isolated immature embryos suitable for genetic transformation or tissue culture, wherein the separated embryos comprise at least some corn embryos suitable for genetic transformation or tissue culture. Separators can work by any suitable mechanism, including, but not limited to, separation by size exclusion, separation based on attractive forces, and separation by mass or density differentials.

Transformed Plants and Methods of their Production

The present invention also provides a transformed monocot plant, produced by the steps including (a) providing at least one transformable target tissue using the methods or apparatuses described herein; (b) introducing a heterologous nucleic acid molecule into the transformable target tissue to produce a transformed explant; and (c) growing a transformed monocot plant from the transformed explant. Preferred monocots of the invention are transformed members of the family Poaceae, including grasses such as turf grasses and grain crops such as corn (maize), wheat, and rice.

Particularly preferred monocot plants include transformed *Zea* species, such as *Zea mays*. Transformed corn preferably contains at least one heterologous nucleic acid molecule capable of conferring a desired trait to the transformed corn, such as herbicide resistance, pest resistance, cold germination tolerance, water deficit tolerance, increased productivity, increased yield, and the like. Practical transformation methods and materials for making transgenic monocot plants of this invention (for example, various media and recipient target cells, transformation of immature embryos, and subsequent regeneration of fertile transgenic plants) are disclosed, for example, in U.S. Pat. No. 6,194,636 to McElroy et al., U.S. Pat. No. 6,232,526 to McElroy et al., United States Patent Application Publication Number 2004/0216189 to Houmard et al., United States Patent Application Publication Number 2004/0244075 to Cai et al., which disclose methods useful with corn, and United States Patent Application Publication Number 2003/0024014 to Cheng et al., which discloses methods useful with wheat, all of which are incorporated by reference herein. Single or multiple heterologous nucleic acid molecules may be used for transforming the monocot plants of the invention; for example, constructs for coordinated decrease and increase of gene expression are disclosed in United States Patent Application Publication Number 2004/0126845 to Van Eenennaam et al., which is incorporated by reference herein.

The seeds of resulting transgenic, fertile plants of the invention can be harvested and used to grow progeny generations, including hybrid generations, of transformed plants that include the heterologous nucleic acid molecule in their genome. Thus, the present invention includes both primary transformed plants ("RO" plants, produced by transforming embryos provided by a method of invention) and their progeny carrying the heterologous nucleic acid molecule. Such progeny transgenic plants can be prepared by crossing a transformed monocot plant of the invention having the heterologous nucleic acid molecule with a second plant lacking the construct. Also, a transformed monocot plant of the invention can be crossed with a plant line having other heterologous nucleic acid molecules that confers another trait to produce progeny plants having heterologous nucleic acid molecules that confer multiple traits.

EXAMPLES

Example 1: Method to Extrude Multiple Corn Embryos

This example shows a method using mechanical positive pressure from an extruder device to produce embryos suitable for tissue culture or genetic transformation.

The tops of kernels were sterily removed from an immature ear of corn (Zea mays) with a common vegetable peeler. The peeler was pushed from the basal end of the corn ear to the apical end using a slight sawing motion to obtain a quick, sharp truncation of the kernels. While in this embodiment the individual kernels are truncated to expose the interior tissues, in other embodiments, it may be necessary only to ensure that an opening (such as a puncture or incision or abrasion) is made in the pericarp without actual removal of pericarp material. Where intact embryos are desired (for example, intact embryos for transformation), the size of any opening is preferably sufficient to allow removal of the embryo without damaging it. Opening of the pericarp can be accomplished by using any suitable device, including, but not limited to, blades and abrasive materials. For example, a vegetable peeler is designed to be relatively safe and fast to use; it has a regulated cutting depth and also requires less skill to use than a scalpel. Other tools with similar functions can be employed. The devices for opening the pericarp are preferably sterilizable, for example, by autoclaving or heating or by chemical sterilization. These pericarp treatment processes can be automated; for example, a blade or blades or abrader can be motorized.

A sterile extruder (in this case, a 4 millimeter diameter rod) was pushed against the base of the truncated kernels. Other suitable extruding devices may be employed. Preferably, such devices should have a size and shape capable of applying a relatively localized force to the base of the truncated kernels to eject the embryos and endosperms. Preferably, the force applied is of sufficient magnitude and is applied in a suitable direction such that the advancing extruder does not "ride up" over the forward kernels. The trailing edge of the extruder preferably also provides a surface on which the ejected embryos and endosperms accumulate; for example, a flat piece of stainless steel with a rounded front edge could be used. In this example, the embryos were gently squeezed out from the pericarp, followed by the endosperms. The extruded embryos and endosperms came to rest on the top of the advancing extruder rod, and were not crushed during the process.

The mixture of embryos and endosperms was washed with an aqueous fluid medium (water, liquid medium, or saline) onto a sterile mesh having diamond-shaped openings (about 2×3 millimeters). The endosperms were observed to be largely retained, and the smaller embryos and some smaller endosperm debris were washed through the screen into a collecting receptacle. The collected embryos were washed twice to remove small debris.

The washed embryos were further purified by a flotation process. In the first step of the flotation process, the aqueous fluid medium was thoroughly withdrawn from the collecting receptacle, which was allowed to dry briefly (for example, about a minute), such that remaining aqueous medium withdrew from the waxy surface of the embryos, exposing them directly to the air. New aqueous medium was added, and the majority of the embryos floated because their waxy surface was not rewetted by the fluid. Non-embryo tissues such as endosperm debris remained submerged in the medium, and a clear separation of embryos and non-embryo tissues was obtained. The flotation of the extruded embryos could be improved by more rapid, complete, or reproducible withdrawal of the aqueous medium, such as through the use of aspiration, or by capillary action (e. g., of a sterile absorbent placed in the collecting receptacle to absorb the fluid away from the extruded embryos).

A yield of approximately 100 embryos was isolated in this preliminary experiment, wherein only a portion of the embryo-endosperm material from the entire ear was processed. These results demonstrate that methods of the present invention are practical and convenient for harvesting large numbers of immature embryos from corn cobs.

The embryos isolated by a method of the invention may then be used in tissue culture procedures, for example, regeneration methods to generate transgenic corn plants. Transfer of the isolated embryos to culture medium was easily done by placing forceps, with the tips closed together, underneath the floating embryos, lifting them free of the liquid with the forceps and placing them on culture medium. Another technique could be to pick the isolated embryos up with an instrument that has a hydrophobic surface. An additional technique would be to transfer embryos by hydrophobicity, for example, transferring them to the medium surface by a small puff of air or sudden mechanical movement, such that their kinetic energy exceeds the hydrophobic force that holds them to the instrument.

Example 2: Visual Confirmation of Embryo Size

This example describes an improvement to one embodiment of the method of the present invention, as described in Example 1. Using the approach described in Example 1, immature corn embryos need to be as close to the truncated part of the kernel in order to be ejected in the greatest numbers. Variation in immature corn embryo size is an important consideration in gauging the amount of kernel top to remove. Embryos tend to be largest in the mid-section of the ear, with somewhat smaller embryos towards the ends. Smaller embryos, e. g., smaller than about 1.5 millimeters in length are more difficult to remove unless they are close to the truncation.

One way to ensure that enough of the kernel has been decapitated above embryos of varying sizes is to observe the cob during the decapitation process under low magnification. For example, low magnification goggles (Donegan Opti-VISOR headband binocular magnifier equipped with a No. 7 lens, which provides a 2.75× magnification) were used to aid visual confirmation of embryo size and suitable truncation of the pericarp. If the first cut did not remove enough of the kernel apex, a second cut could be made. Other low magnification devices, using the same or similar magnifications could be used. For example, available lenses for the Opti-VISOR provide magnification ranging from 1.5 to 3.5×.

Example 3: Extrusion of Embryos and Endosperms

This example describes an improvement to one embodiment of the method of the present invention, as described in Example 1. Powered devices may be used to assist in the extrusion of embryos and endosperm. For example, a power chisel such as a WeCheer 320 power chisel, fitted with a rounded extruder device, can be used to reduce the force a person needs to exert to eject the embryos and endosperms. Other powered devices are available and can be similarly used. Preferably, the "chisel" portion of such a tool (or any part of the tool that might come into contact with the embryos) can be conveniently sterilized, for example, by insertion into a bead sterilizer.

In one experiment, the blade of a stainless steel weighing spatula was bent back on itself to provide an extruder device having a rounded leading edge. After insertion into a WeCheer 320 power chisel, a portion about 10 centimeters long extended out from the power chisel's chuck. This assembly was used to eject the embryos and endosperms from individual rows of decapitated kernels. As the extruder device (modified spatula) moved down a row of kernels, a slight tendency for the spatula to slide off center to the left or right was observed; however, this tendency could be corrected by including a small keel-like extension of the spatula on each outer edge.

Example 4: Mechanized Embryo Extrusion

This example describes an improvement to one embodiment of the method of the present invention, as described in Example 1. Mechanization of the embryo extrusion process can be achieved by use of a suitable device, such as, but not limited to, the device described herein and schematically diagrammed in FIG. 1. This device includes two motors. The first motor D is a stepper motor that can rotate the corn ear so that new rows of kernels are exposed to the two extrusion rods G, which apply force to squeeze the embryos and endosperms out of their pericarps.

Rods G are conveniently located on opposite sides of the ear in order to balance the pressure applied to the ear relative to the ear's longitudinal axis. However a single rod can be used, or more than two rods; where multiple rods are used, it is preferable that they are positioned so as to evenly distribute the resulting mechanical pressure around the ear. The rod need not be a straight rod; in one embodiment of the device, a flexible "collar" encircling the circumference of the ear is used instead of a rigid rod. In another embodiment, multiple short rods or rollers are arranged in a flexible, circular configuration that can be slid along the ear's longitudinal axis, applying mechanical pressure to many or all rows of kernels simultaneously.

The second motor is connected to the pinion gear E connecting to a rack F so that up and down linear motion of the ear occurs. The base of the ear is held firmly to a handle B by means of a screw extending from the handle down into the base of the ear. The narrowed middle portion of the handle is square so that it will not rotate unless the holder C to which it is attached is rotated by the stepper motor D.

Before insertion into the machine, the tops of the kernels are decapitated as in Example 1 so that the embryos and endosperms can be squeezed out. To start the process, the ear is lowered until the two rods G are near the base of the ear just below the handle B. Then the rods are pressed against both sides of the ear and the rack and pinion assembly draws the ear upward. As this happens, the embryos and endosperms are removed from a couple of rows, fall downward into the collection dish H resting on the base I, and collect in a pile J. When the rods approach the apical end of the cob, the cob is withdrawn upward to its original starting position and rotated slightly by the stepper motor until new rows of kernels come into position.

Various degrees of automation of this machine are possible, including sensors to automatically adjust the vertical starting and finishing positions as well as the rotary start and finish positions. A rack and pinion is not the only method by which linear motion can be obtained. Pneumatics or hydraulics may be preferred for some applications. Rods G can be automatically opened by a suitable mechanism. When a new ear is loaded, it may be preferable to raise the ear to a position high enough to clear the rods.

Example 5: Hydrophobic Separation of Embryos

This example describes an improvement to one embodiment of the method of the present invention, as described in Example 1. In separation applications the material of interest frequently appears at the interface of dissimilar phases (for example, between aqueous and lipophilic solvents). Removing the material of interest from such an interface can pose problems, and has in the past been a manual process involving close contact with the extractant and the material to be extracted. Often the only way to successfully separate out a component is to use a material of the same polarity or hydrophobicity/hydrophilicity. In the case of immature corn embryos extruded by a method of the invention, the embryos are found at the aqueous/air interface. The corn embryos' surface is waxy, i. e., lipophilic or hydrophobic, and when an embryo cuticle is contacted with a substance of similar hydrophobicity, the embryo will tend to stick to the hydrophobic surface. The embryo's hydrophobicity reduces the surface tension of the water around it, which helps the embryo to "float" at the surface of the aqueous/air interface.

One approach that takes advantage of these physical characteristics would be to touch the floating embryos with a hydrophobic material (such as hydrophobic filter paper, e. g., Whatman No. 1 PS paper, which is a water-repellant phase separating paper impregnated with silicone; see, for example, www.whatman.com/repository/documents/s3/tech_appli_010.html). In one example, a piece of sterile hydrophobic filter paper can be lowered onto an entire container of floating embryos and pick them all up at once. In another example, a small piece of the hydrophobic paper can be used to successively pick up a number of embryos and transfer them to the next container. In a third example, either a small piece of the hydrophobic paper or a hydrophobic pipette tip would be used to contact and pick up individual embryos and then dispense them, with a puff of air from the pipettor. Ordinary pipette tips could also be modified for such use by inserting a pipette tip into a short length of hydrophobic tubing (for example, silicone tubing); the embryo could then be picked up by hydrophobic attraction to the distal end of the hydrophobic tubing, and then released by dispensing a puff of air from the pipette. Reduced surface tension around the hydrophobic embryos helps them float on an aqueous surface, and the floating embryos could also be transported by moving them on the aqueous surface (for example, by an air jet directed at the embryos). Picking up and dispensing of embryos can be automated using modifications of existing devices, such as machines designed for colony picking or for retrieving protein spots on stained 2-D protein gels.

Example 6: Further Methods of Ejecting or Extruding Embryos

The method of the present invention encompasses the use of various types of force, or combination of forces, for separating the embryo from its seed. This example describes further embodiments. In one basic method as described in Example 1, mechanical positive pressure is applied to the base of a truncated seed (such as a corn kernel) to eject the embryo out through the truncated top of the seed.

In another embodiment, centrifugal force can be used to eject the embryo. For example, a corn ear (the kernels of which have previously been truncated) could be spun about its longitudinal axis at a speed sufficient to eject the embryos and/or endosperms in a radial trajectory. Spinning could be achieved by any suitable technique, such as, but not limited to, contacting the apical end of a corn ear with a freely rotating cone, wherein the rotation of the ear is kept within a limited longitudinal range, for example, by attaching the basal end of the ear to a handle which is then inserted in a holder within which it can rotate. In one exemplary embodiment using centrifugal force, about a third of the top of each kernel on a corn ear was removed with a scalpel, and the ear rolled on a surface to loosen the embryo and endosperm within the kernels. The ear was snapped into two pieces, each about 750 millimeters in length. Each piece was placed in a 250-milliliter centrifuge bottle with about 100 milliliters of water. These were centrifuged 15 minutes at 5000 rpm to eject the embryos. Examination of the ears after centrifugation showed that, in some portions of the ear, all the embryos had been removed by the centrifugation, whereas in other areas, few or no embryos were removed. The ejected material was centrifuged and the supernatant removed to leave a slurry, which contained intact embryos (estimated to include about 20 percent of the total number of embryos). In another example, an immature ear of corn is harvested (typically between about 10 to about 14 days post-pollination). The ear is disinfested, and under sterile conditions the top of each kernel is cut off. The ear is mounted on a drill bit on an electric drill (or a similar device) and the ear is surrounded by a large sterile collection vessel (e. g., a large glass beaker). The ear is spun at a rotation sufficient to eject the immature embryos, and the ejected tissues are collected from the sterile container. Immature embryos are collected, for example, by manual collection, or by rinsing the container with sterile tissue culture medium and recovering an enriched fraction containing the embryos (e. g., by sieving, by the use of a liquid density gradient, or by other methods to separate embryos from non-embryo tissues as described elsewhere in this disclosure). The immature embryos (or callus derived from the immature embryos) can be used subsequently for transformation. Improved results using these and other centrifugation methods can be obtained by determining preferred centrifugation times and speeds by routine testing.

Another embodiment employs bulk maceration of kernels. An immature ear of corn is harvested (typically between about 10 to about 14 days post-pollination). The ear is disinfested. The pericarp can be opened under sterile conditions or the kernels can be left intact. The kernels are removed from the cob by any suitable procedure, including, but not limited to, using a scalpel or other bladed tool. The kernels, once separated from the cob, are placed in tissue culture medium. The kernel-medium mixture can be subjected to further tissue disruption using a suitable cutting device, such as, but not limited to, a blender. Immature embryos are collected, for example, by manual collection, or by rinsing the container with sterile tissue culture medium and recovering an enriched fraction containing the embryos (e. g., by sieving, by the use of a liquid density gradient, or by other methods to separate embryos from non-embryo tissues as described elsewhere in this disclosure). Immature embryos (or callus derived from the immature embryos) can be used subsequently for transformation.

In a further embodiment, fluid jets (of gases or liquids or combinations thereof) could be used to dislodge embryos. One example of this approach is to automatically rotate a corn ear in a stepwise or continuous (helical) manner past a stationary jet, collecting the ejected material containing the embryos and further isolating the embryos if necessary, for example, by size separation on a mesh or screen or the like. Where the corn ear is vertically orientated (with respect to its longitudinal axis), it may be preferred to rotate the ear in an upward helical direction, or otherwise move the ear relative to the jet so that extracted embryos tend to wash downward.

In yet another embodiment, linear deceleration or linear acceleration could be employed to dislodge or eject the embryos. For example, a corn ear could be administered a shock parallel to the ear's longitudinal axis and of sufficient force to eject the embryos and endosperms. A corn ear could be enclosed in a suitable sterile, high impact-resistant holder, which could be subjected to sudden acceleration or deceleration, for example, by a sharp impact (e. g., as from a mallet).

Another improvement to the method would be to facilitate ejection or extrusion of the embryo from the truncated seed. For example, embryos could be loosened or dislodged within their native position within the seed by applying a force to the tops of intact seeds (e. g., by applying a roller or other means of applying pressure to the tops of rows of corn kernels in an intact ear or rolling or pressing the ears themselves on a surface prior to decapitating the tops of the kernels). Embryos may also be loosened within the seed by application of vibration, for example, by ultrasound. Another approach would be to remove additional non-embryo tissue, such as additional lateral wall (pericarp) material, before embryo ejection or extrusion. For example, a V-shaped knife or other instrument could be used to remove some of the lateral walls of corn kernels in rows in the ear.

Example 7: Automated Embryo Isolation Using Fluid Jet Positive Pressure

Figure 2:
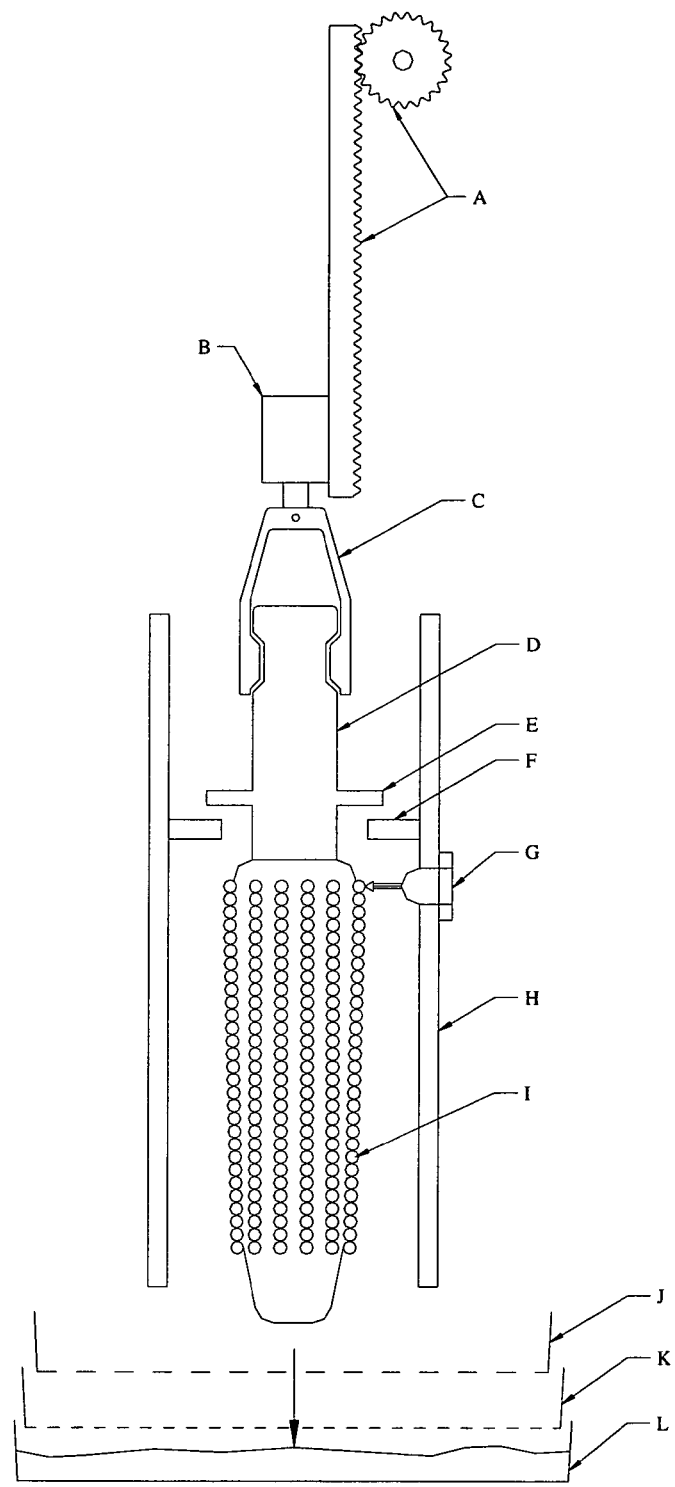
FIG. 2 depicts one embodiment of an apparatus of the present invention that uses fluid jet positive pressure to dislodge embryos from seeds by a method of the invention, as described in Example 7. Legend: (A) robot with motion in X, Y and Z dimensions, (B) motor to rotate corn ear, (C) grasper, (D) handle to hold corn ear, (E) baffle to prevent material from splattering upwards, (F) flange to prevent material splattering upwards, (G) aperture for guiding fluid, (H) transparent tube, (I) corn ear, (J) shaking screen, (K) cheesecloth or other porous material, and (L) waste container.

This example describes a further embodiment of the present invention. In this example, an automated device uses fluid jet positive pressure to dislodge embryos from seeds. With reference to FIG. 2, a robotic grasper C (preferably capable of motion in three dimensions by means of robot A and motor B, or by an equivalent means) picks up a corn ear I (by a handle D having a baffle E) in a defined position for a rack on the robot deck. The robot inserts the corn ear into tube H (optionally made of transparent material for ease of visual observation) at a starting position below flange F. Fluid jet positive pressure is introduced through aperture G and the ear is simultaneously raised (in the Y dimension) and rotated by robot A and motor B, preferably resulting in each kernel being struck by the fluid jet, causing the embryo and endosperm to be dislodged. The fluid passing through aperture G can be at least one gas, at least one liquid or any combination thereof. The fluid jet can exert force continuously or non-continuously, for example, as in pulses. As the embryos and endosperms are dislodged by fluid jet positive pressure from aperture G, they fall down to the shaking screen J, which retains the endosperms while permitting the embryos to fall through to the collecting surface K (for example, sterile cheesecloth) below. Excess fluid can be optionally collected in waste or recycling receptacle L. After completion of the embryo removal process for each corn ear, the interior of the tube can be briefly washed down manually or by automated jet above or below the flange F.

Example 8: Methods of Processing Crude Embryo Preparations

The embryo preparations obtained by methods such as those described in Examples 1 through 7 may include both intact embryos and partial embryos, which may be accompanied by non-embryo tissues, such as endosperm and glumes. Some applications may not require further treatment or separation steps, for example, in a mass transformation of such a "crude" embryo preparation where embryos (intact or partial) need not be separated from non-embryo tissue. For example, callus derived from either intact or partial immature corn embryos can be used for transformation, regeneration, and production of fertile, transgenic plants. Thus, both intact and partial embryos may serve as transformable explants and need not be separated from each other. However, in other cases it may be desirable to further purify embryos from a crude embryo preparation.

Procedures wherein some difficulties may be encountered in processing crude embryo preparations include: (1) rinsing away of non-embryo tissue (e. g., cell debris, starch grains, undesirable proteins), (2) efficiently removing excess liquid from embryos after extrusion or rinsing using liquid, and (3) adding liquid with minimal turbulence so that the embryos float and do not become submerged.

A porous material is useful for separating non-embryo tissue from embryos. Any suitable porous material can be employed, preferably having a mesh or hole size small enough to retain embryos but let smaller, non-embryo tissues or debris pass through, and capable of being sterilized (e. g., by autoclaving, heat, irradiation, or chemical sterilization). Suitability of materials is easily judged or tested by simple experimentation by one skilled in the art. Examples of suitable materials include cheesecloth or other woven material, and other meshes or screens. In some embodiments, perforated solid materials can be used, including perforated ceramics, polymers, metals, or glasses (for example, in the form of a Buchner or similar separatory funnel). Cheesecloth of appropriate gauge, for example, has a mesh size small enough to retain embryos but allows smaller debris to pass through, and is autoclavable. Cheesecloth can be attached to a frame or collar (for example, the frame holding embryo collecting surface K in FIG. 2 and described in Example 7) to allow the cheesecloth and all the retained embryos to be simultaneously submerged for easy rinsing. For example, cheesecloth can easily be attached to the frame by means of an elastic band or the like (e. g., silicone tubing); such frames are easily manufactured, for example, from a beaker or graduated cylinder made of autoclavable material (e. g., polypropylene, polymethylpentene, polycarbonate, or autoclavable glass) cut into sections. Cheesecloth has strong capillarity, allowing liquid to be efficiently pulled away from the embryos, thus exposing their waxy epidermis to air prior to flotation. In the flotation step, the cheesecloth is simply submerged in aqueous liquid, allowing the embryos to float off.

Example 9: Substantial Isolation of Embryos Using a Fluid Jet

This example describes a further embodiment of the present invention. In this example, multiple embryos were dislodged from seeds by fluid jet positive pressure.

In the simplest example, a 200-microliter pipette tip was attached to a vertical sink nozzle with Parafilm®. When the tap water was turned on a jet emerges from the pipette tip with considerable force. The tap water pressure was estimated to be about 60 pounds per square inch. This fluid (liquid) jet was trained on an immature corn ear (contained in a beaker) wherein the kernels had been decapitated as described in Example 1. As the jet stuck each kernel, the endosperm and embryo were ejected, and collected in the beaker. Since the endosperm at this stage is a relatively soft tissue it was fragmented into many smaller pieces by the jet, whereas the embryos appeared to remain intact.

The endosperm and embryo tissue dislodged by the jet was poured directly onto a No. 60 cheesecloth (other suitable porous material, such as hydrophilic mesh of the appropriate mesh size, could be substituted). Different "grades" of cheesecloth are available (for example, grades 10, 20, 30, 40, 50, 60, 70, 80, and 90, where the mesh openings decrease with higher grades), and the grade or mesh size appropriate to the average size and shape of a given type of embryo is easily selected by simple experimentation. The embryos and larger fragments of the endosperm were retained on the upper surface of the cheesecloth. Prior to the next step, the cheesecloth was allowed to partially dry by wicking away excess liquid. This pulled liquid away from the tissues and exposed the surfaces of the embryos to air. When the cheesecloth was lowered into aqueous liquid, the embryos floated because their waxy epidermis did not rewet.

In a simple set up, the cheesecloth (or other suitable porous material) can be manually stretched or held over a receptacle or waste container as the liquid holding the crude embryo preparations is poured through the cheesecloth. For sterile work, the cheesecloth can be attached to rigid frames, which can be autoclaved before use. Snap-together sieves with handles, such as those available in kitchen supply stores, could also be used in the method.

Example 10: Devices for Embryo Extraction Using a Fluid Jet

This example describes various embodiments of an apparatus for mechanically preparing multiple corn embryos suitable for tissue culture.

One embodiment includes an apparatus for preparing multiple corn embryos using a fluid jet, generally similar to the device depicted in FIG. 2. A transparent, open-ended cylinder was made by cutting the ends off a 1-liter autoclavable polymethylpentene (PMP) graduated cylinder. A pipette tip (1250-microliter Gilson Distritip, tapered to avoid backpressure build-up) was secured to the side of the cylinder and served as an aperture for guiding a fluid stream as a jet through a hole made in the cylinder's wall. Fluid (in this case, water) was fed through the pipette tip from PharMed® high pressure autoclavable peristaltic pump tubing; the water was delivered from a laboratory sink tap, but could be an aqueous fluid delivered from a pump or other source. Using a pump capable of delivering a sterile fluid is preferable when, for example, sterile culture medium or a sterile salt solution is found to be superior to water as a liquid for substantial isolation of embryos. An example of a suitable pump is a Masterflex pump with the high pressure L/S pump head, which can deliver sterile liquid at up to 100 psi when used with high pressure tubing.

A corn ear with previously decapitated kernels was manually positioned within the cylinder. Once the ear was positioned appropriately within the cylinder, each kernel was subjected to positive pressure from the water jet. This resulted in the embryos and non-embryo tissues being extruded from the kernels. Examination of the ear after this treatment indicated efficient removal of the embryos from the kernels. The extruded material was washed down the cylinder's interior walls to an embryo collector positioned beneath the cylinder. The embryo collector included: (1) a coarse plastic screen (onto which larger debris was trapped), heat-fused to the cut-off top of a Tri-Pour™ plastic beaker and stacked above (2) a finer screen (Grade 60 cheesecloth, onto which the extruded embryos were trapped), secured with an elastic band to the cut-off top of a second Tri-Pour™ plastic beaker and stacked above (3) a waste collection beaker or other container (in which the fine debris, non-embryo tissues, and waste liquid was collected).

Figure 3:
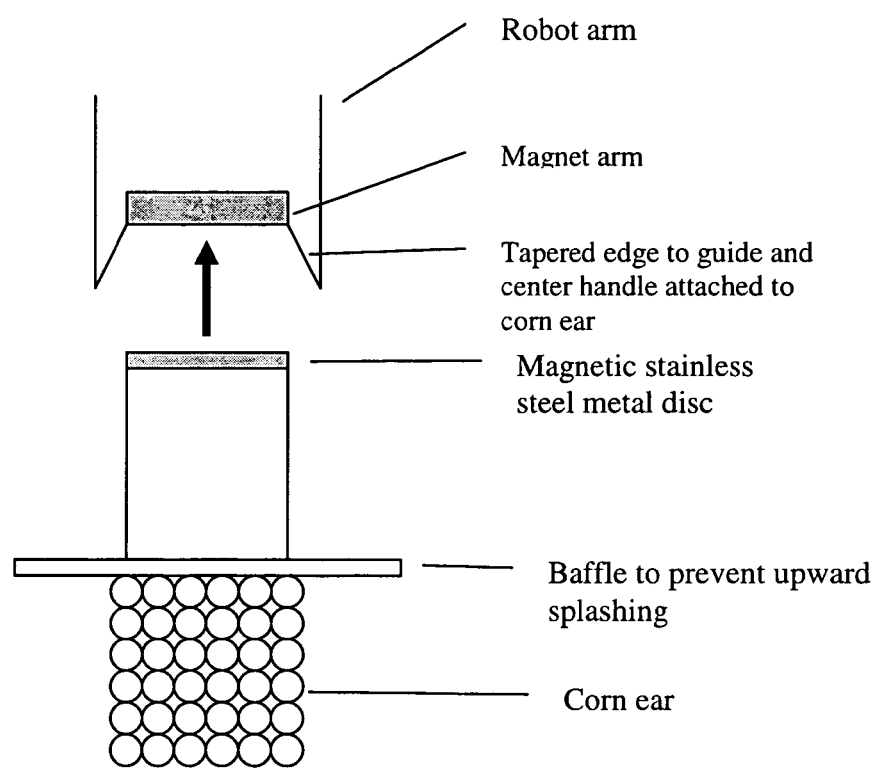
FIG. 3 depicts one embodiment of a mounting mechanism using a magnetic "handle" by which a corn ear can be secured to a robot arm, as described in Example 7.

Modifications to these and similar embodiments are easily made by one versed in the art. For example, with regard to positioning the corn ear or seed for application of the fluid jet, the ear could be held manually in place, or preferably, mounted securely within the cylinder by a movable support capable of moving the ear in three dimensions. For example, the ear could be mounted to a threaded metal or polymer rod, such as a polypropylene rod, which could be used to move the ear along its longitudinal axis as well as to rotate the ear). Another example of a mounting mechanism is depicted in FIG. 3, which illustrates a magnetic "handle" by which an ear can be secured to a robot arm.

In other embodiments, however, the corn ear or ears need not be individually secured to a holder but can be freely movable so as to allow multiple kernels to be contacted by the force used to remove the embryos from the kernels. For example, at least one ear, or multiple ears, can be borne on or held between at least one support, such as, but not limited to, at least one plane, frame, grid, screen, mesh, platform, roller, guide wire or rod, and belt, wheel, or roller conveyor. Such a support could be movable or could cause the ear or ears to move, for example, by vibration, rolling motion, gravity, or other mechanisms. Substantially isolated embryos could pass through the platform itself if the platform was porous (e. g., made of mesh). The ear or ear can also be floated on a fluid in a manner allowing each ear to rotate or otherwise move freely while afloat. The fluid, such as a liquid containing the substantially isolated embryos, could be continually drained off, optionally through a filtering or sedimenting device, or collected for centrifugation.

Devices for obtaining motion along the longitudinal axis of a corn ear include, but are not limited to, ball screw-driven slides or belt-driven slides, such as those commercially available from various manufacturers such as Techno, Inc. (techno-isel.com). To obtain rotary motion for rotating a corn ear, a stepper motor can be used, for example, a stepper motor attached to a slide plate. Rotary motion can also be provided by rolling devices, for example, by parallel round or tubular rollers between which the corn ear is held and rotated.

The shape of the fluid jet can be advantageously modified according to the desired application. For example, a narrow column-shaped jet of uniform diameter is useful for removal of embryos from one seed at a time. Where it is desirable to increase the rate at which embryos are substantially isolated, multiple embryos can be simultaneously removed from their seed by a fluid jet; this can be achieved, for example, by using at least one single fluid jet that covers a larger area, or by using multiple jets simultaneously. In one embodiment, multiple jets, such as multiple parallel, narrow, column-shaped jets (for example, produced by multiple nozzles similar to that used in Example 9 and optionally connected to each other by a manifold) are used to direct fluid jet positive pressure on multiple seeds to substantially isolate their embryos substantially simultaneously. Automation of these and other devices can further include optical or mass sensors to aid in positioning the ear and fluid jet relative to each other.

In another embodiment, at least one fluid jet that covers a larger area (for example, wherein the fluid jet simultaneously impacts multiple kernels, or multiple rows of kernels on a corn ear) can be used. The dimensions of such a jet preferably allow the jet to enter the kernels and wash out the embryo. Typically, corn embryos used in genetic experiments are immature and generally in the size range of about 1.8 to about 2.2 millimeters in length; the kernels holding these immature embryos are generally in the size range of between about 4 and about 5 millimeters in width. For embryos of this size, an appropriate fluid jet can be, for example, between about 0.5 to about 1 millimeter in width.

Figure 4:
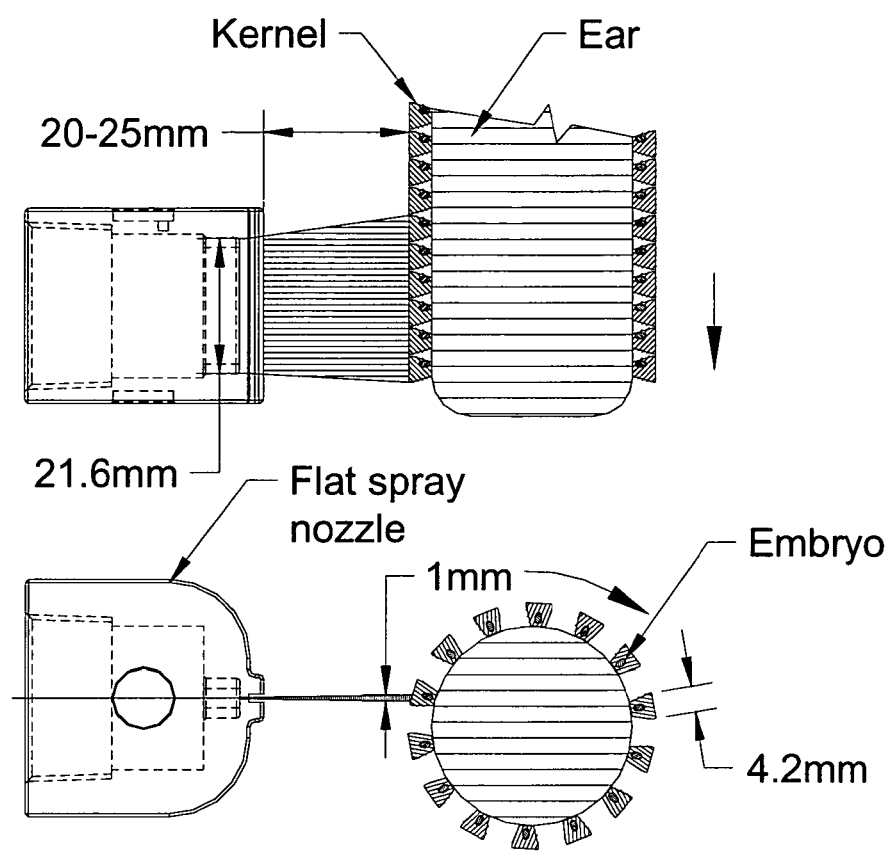
FIG. 4 depicts one embodiment of a nozzle useful in methods of the invention, as described in Example 7. This nozzle generates a substantially uniform, flat sheet-like jet of fluid.

Any suitable means for producing such a larger fluid jet may be used, such as, but not limited to nozzles that generate non-columnar fluid jets. Examples of suitable nozzles include, but are not limited to, nozzles that generate a flat spray pattern and nozzles that generate a fan- or a cone-shaped spray pattern. In one example, a commercially available flat spray nozzle (number 23990-1/4-04, Spraying Systems Co., Dillburg, Pa.) was used with a Masterflex L/S pump (model 77250-62) to pump liquid at 1 liter per minute and 30 psi; embryos were excised from a corn ear under these conditions. Another example of a preferred nozzle is a nozzle that generates a fluid jet in the form of a flat "sheet" of fluid, such as is depicted in FIG. 4. Such a nozzle preferably is capable of generating a uniform, flat fluid jet that maintains a coherent, uniform sheet-like flow for at least a distance sufficient to allow the flow to contact more than one seed (and preferably several seeds) at the same time. The novel nozzle depicted in FIG. 4 is designed to generate a uniform, flat sheet-like jet that is about 0.5 to about 1 millimeter in thickness, greater than about 20 millimeters in width, and maintains the sheet-like flow over a distance of about 20 to about 25 millimeters from the nozzle's aperture. This latter distance permits the jet to be moved along the rows of kernels with minimal adjustment needed for differences in distance between the surface of the kernels and the nozzle's aperture.

Regardless of the area or shape of the jet or spray pattern generated by the nozzle or aperture through which the liquid flows, nozzles or apertures are preferably used with flow rates and pressures sufficient to generate enough fluid force to dislodge the embryo from its seed, without damage to the embryo. In some embodiments, it is preferable to use a lower flow rate and possibly a higher pressure, to minimize consumption of fluid (such as medium) as well as to minimize the waste generated.

Example 11: Using a Gas Jet to Substantially Isolate Embryos

This example describes further embodiments of methods and devices for mechanically preparing multiple corn embryos suitable for genetic transformation or tissue culture. As described in Example 6, gas jets can also be used for the substantial isolation of multiple embryos. An apparatus similar to that described in Example 10 was modified for use with gas. A 1-milliliter pipette tip (catalogue number TN1300RS, Marsh Bio Products) was secured to the side of the cylinder and served as an aperture for guiding a stream of air as a jet through a hole made in the cylinder's wall. Air was supplied from a compressor pressurized to between about 60 to about 100 psi. An air valve for convenience was positioned in line between the compressor and the pipette tip. The air jet emerging from this pipette tip was used to dislodge the embryos from a prepared corn ear. Examination of the kernels after they had been subjected to the air jet showed that the thick pericarp remained in place and surrounded by papery glumes, and the pericarp contents (embryo and endosperm) had been removed. Examination of the tissue retained by the grade 60 cheesecloth showed that this included dislodged embryos as well as some glumes dislodged by the high-pressure air jet. The glumes of corn have a waxy surface like the embryos and also float following the flotation procedure. Using lower air pressures can reduce glume contamination.

Example 12: Substantial Isolation of Embryos Using Other Fluid Forces

This example describes further embodiments of methods and devices for mechanically preparing multiple corn embryos suitable for genetic transformation or tissue culture. Forces exerted by fluids, other than positive fluid pressure from a fluid jet, can be used to substantially isolate embryos. In one experiment, the tops of kernels were removed from a corn ear, which was placed inside a bottle containing sterile distilled water and shaken vigorously by hand. This resulted in the substantial isolation of 90 out of the ear's 200 embryos. Another experiment repeated the preceding procedure except that the shaking was carried out in a mechanical paint shaker. In this experiment, 56 embryos were substantially isolated out of the ear's 190 embryos. In a third experiment, a similar procedure was carried out, except that the corn ear was pre-soaked in 211 medium, and the shaking was carried out in a paint shaker. In this experiment, 109 embryos were substantially isolated out of the ear's 210 embryos. In these cases, non-jet fluid force from movement of the liquid around the corn ear resulted in the substantial isolation of the embryos; the fluid force could include fluid turbulent flow, fluid laminar flow, shear from fluid flow, negative fluid pressure (for example, resulting cavitation), or combinations thereof. Forces can also include forces generated by acoustic techniques, such as by an acoustic wave or waves (pulsed or continuous) in either gas or fluid phase.

Preceding examples (including Examples 9-11) described use of a fluid jet to remove embryos from an immature ear. During these procedures, it was observed that the fluid jet generally also caused at least part of the endosperm to be released from the kernel. The endosperm tissue was observed to be softer and more friable than the embryos, and tended to disintegrate to varying degrees (in contrast to the embryos, which tended to remain intact). It is possible that the endosperms disintegrate upon exposure to shear caused by the fluid jet. This shear is believed to be non-uniform, resulting in the variability in disintegration observed; nonetheless, a large proportion of the endosperm material that was sufficiently disintegrated to pass through the cheesecloth, leaving a retentate made up of a semi-pure preparation of embryos.

When a low-pressure jet from an ordinary laboratory squirt bottle was directed at the cheesecloth retentate, more of the remaining endosperm tissue was disintegrated further and washed through the cheesecloth, leaving behind a relatively more pure preparation of embryos. Thus it is reasonable to predict that if the retentate is uniformly exposed to a shear force of the correct intensity, all or substantially all of the remaining endosperm should disintegrate and pass through the cheesecloth. Such a shear force could be generated by any suitable means, such as, but not limited to, a single jet, multiple jets, a sheet-like or curtain-like jet, rapidly moving jets, and acceleration or deceleration of the endosperms. Additionally, if the jet used to initially release the kernel contents is designed to expose a higher proportion of the endosperms to shear during ejection, an initial higher purity embryo preparation could be obtained.

One non-limited embodiment of applying shear to further purify embryos follows. Once the embryos and partially disintegrated endosperms are released from a cob, the remainder of the endosperm can be rapidly fragmented by fluid flow, for example, from a spray nozzle, that strikes the endosperm uniformly and simultaneously. One suitable type of nozzle is a full cone nozzle. Full cone nozzles generate a spray pattern completely filled with drops. An internal vane within the nozzle imparts controlled turbulence to the liquid prior exiting to the orifice, allowing formation of the spray pattern. Commercially available nozzles have spray patterns that are round, square, or oval. An example of a suitable full cone nozzle is known as "UniJet Spray Nozzle, Standard Spray, Small Capacity" (part number TG-SS0.3, MANUFACTURER/LOCATION?).

Example 13: Combination Devices

This example describes several additional embodiments of the method of the invention, which use a combination of forces to substantially isolate multiple embryos from seeds.

Figure 5:
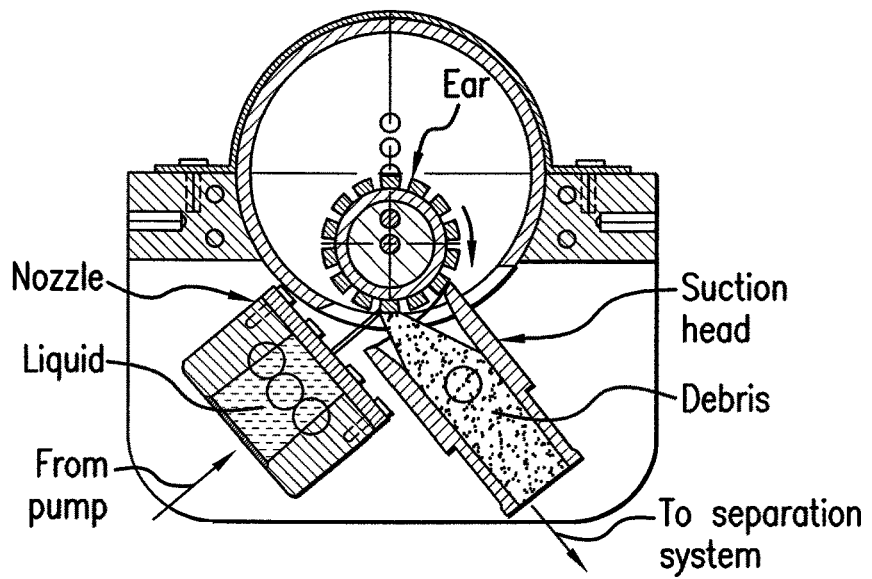
FIG. 5 depicts one embodiment of an apparatus useful in methods of the invention, as described in Example 13. This device includes a nozzle for generating a substantially flat fluid jet and an optional suction head.
Figure 5:
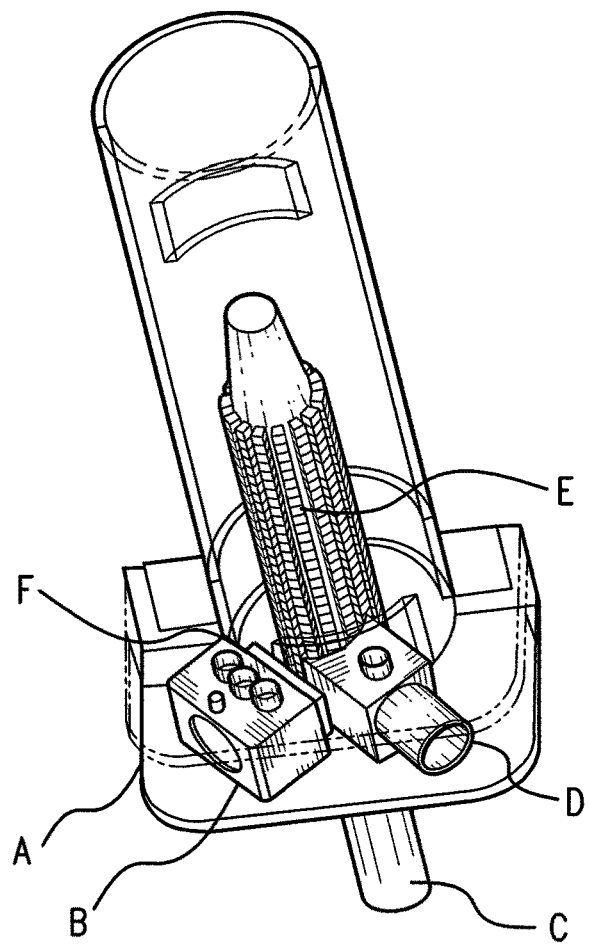

FIG. 5 illustrates a device using a larger fluid jet (as described in Example 10). This device includes a nozzle for generating a fluid flow such as a larger fluid jet (for example a flat fluid jet), and, optionally, a suction head, or component for applying negative fluid pressure (e. g., by vacuum or suction), for dislodging embryos and/or for collecting the dislodged embryos. FIG. 5 (top) depicts a cross-sectional view of an example of such a device, showing how the nozzle, optional suction head, and corn ear can be positioned relative to each other. The corn ear, nozzle, and optional suction head can be moved relative to each other; for example, the corn ear may be stationary while the nozzle and optional suction head are moved, or the nozzle and suction head may be stationary while the corn ear is moved. FIG. 5 (bottom) schematically depicts a corn ear positioned in the device, and shows the nozzle positioned to generate a flat fluid jet wherein the jet impacts multiple kernels in a row.

Figure 6:
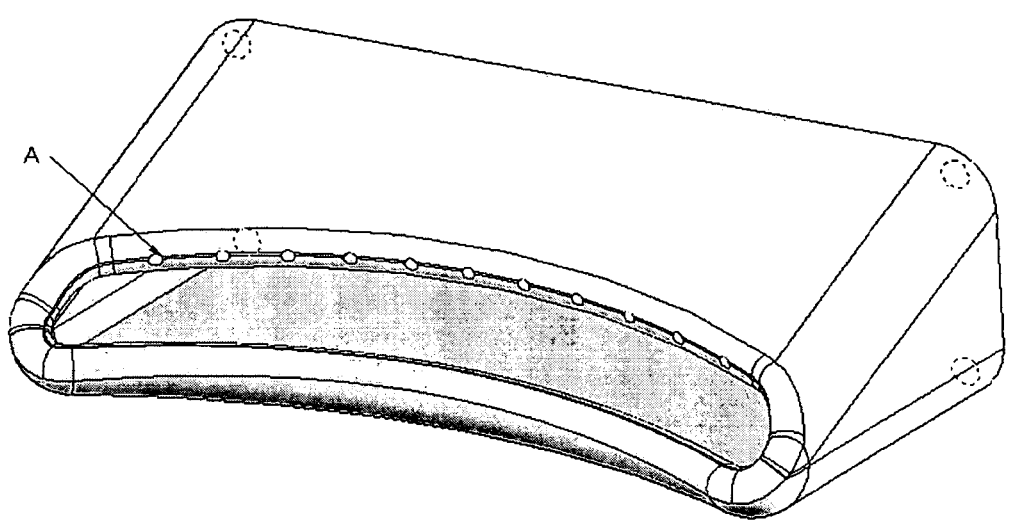
FIG. 6 depicts one embodiment of a component useful for applying negative fluid pressure useful in methods of the invention, as described in detail in Example 13. Legend: (A) one or more apertures for guiding fluid flow.

FIG. 6 depicts an embodiment of a suitable suction head or component for applying negative fluid pressure (e. g., by vacuum or suction), such as is optionally used in the device of FIG. 5, and which can also be used on its own to substantially isolate embryos. The suction head can include one or more apertures through which negative fluid pressure can be applied. The suction head can also include a means for dispensing fluid (such as gas or liquid, e. g., water or medium), for example, multiple apertures in the suction head. For use with corn, the suction head is preferably shaped to follow the contours of a typical corn ear, and is preferably capable of entrapping embryos from multiple kernels or from multiple rows of kernels. It is envisioned that the suction head can be manufactured of a rigid material (such as stainless steel or other metals), or of a flexible material to allow easier conformation of the suction head to the contours of a corn ear, or of combinations thereof. Embryos can be substantially isolated by any combination of mechanical positive pressure (exerted, for example, by a leading edge of the suction head), negative fluid pressure (e. g., suction or vacuum), and fluid force (such as, but not limited to, positive pressure from a fluid jet, fluid turbulent flow, and fluid laminar flow entrapping material from the interior of the kernel)

Devices for applying force for substantially isolating embryos, such as are described in Examples 1, 3, 4, 6, 7, 9, 10, and the present example (including, but not limited to the devices illustrated in FIGS. 5 and 6) can be moved relative to the corn ear. The ear may be stationary, or the device may be stationary, or both can be moved. Because corn seed typically occurs in relatively uniform rows arranged parallel to the longitudinal axis of the corn ear, the device is typically moved (relative to the ear) so that the device passes parallel to the longitudinal axis of the corn ear and following a row or multiple rows of kernels. However the motion of such devices relative to the ear can follow the circumference of the ear, or can be random, or can be any combination of suitable motions.

Figure 7A:
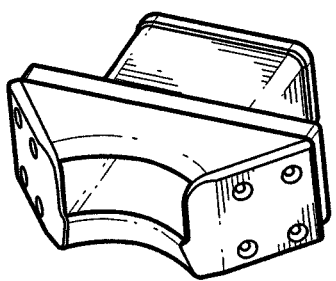
FIG. 7A through 7C depict different views of an embodiment of a device that uses a combination of forces and is useful in methods of the invention, as described in detail in Example 13. This device includes a head with a leading edge capable of applying a predefined amount of mechanical pressure to the base of kernels that previously have had the pericarp opened or truncated and a component for applying negative fluid pressure. This device can further include a means for dispensing fluid or for guiding fluid flow.
Figure 7B:
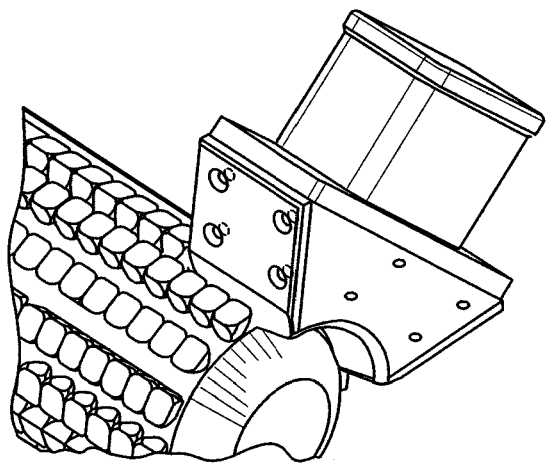
Figure 7C:
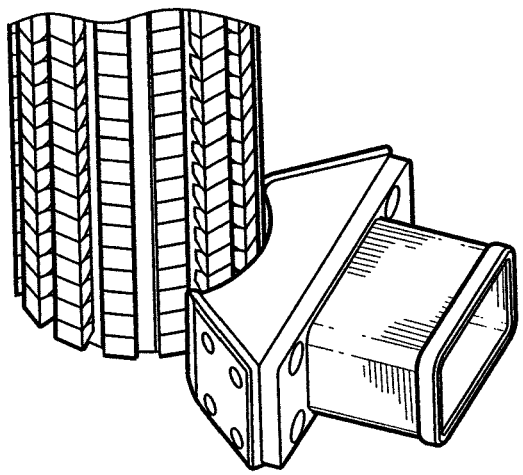

FIG. 7A through 7C depict different views of an embodiment of a device that uses a combination of forces to substantially isolate multiple embryos from seed (in this example, corn). This device includes a head with a leading edge capable of applying a predefined amount of mechanical pressure to the base of kernels that previously have had the pericarp opened or truncated, so that the embryos are extruded from the kernels in a manner similar to those described in Examples 1, 3, and 4. The device further includes a component for applying negative fluid pressure (e. g., by vacuum or suction) for dislodging embryos and/or for collecting the dislodged embryos. The extruded embryos (and accompanying non-embryo tissues) are thus separated from the corn ear and can be collected by application of negative fluid pressure. The collected embryos and non-embryo tissues can be further separated, if desired, by suitable means, such as by size-separation, hydrophobic separation, or differential centrifugation. A variation of this device could include a means for dispensing fluid (such as liquid, e. g., water or medium), for example, multiple apertures in the suction head.

The embryo extraction devices depicted in FIGS. 5, 6, and 7 are described as illustrative examples that are not intended to be limiting. These and other such devices can include additional components, for example, means for separating the embryos from non-embryo tissues or from fluids used in the substantially isolation process.

Example 13: Viability Data

The multiple monocot embryos provided by use of the methods and devices of the present invention are most preferably embryos suitable for genetic transformation or tissue culture application such as transformation and regeneration of plants. This example further illustrates the utility of methods of the invention in providing multiple monocot embryos that are viable and suitable for genetic transformation or tissue culture. In this example, the quality of immature corn embryos obtained by different excision methods was compared in their response to transformation by *Agrobacterium tumefaciens*.

For transformation, a plasmid containing left and right border sequences, a gene for glyphosate resistance for selection, and a reporter gene (gfp, encoding green fluorescent protein) was used. *Agrobacterium* containing this plasmid was streaked from a frozen glycerol stock onto an LB plate and grown for 3 days in a 28 degree Celsius incubator. A seed culture was prepared by inoculating three colonies from the LB plate into 25 milliliters of LB broth, which was incubated 15 hours at 27 degrees Celsius with shaking (200 rpm). This seed culture (10 milliliters) was diluted with 40 milliliters of fresh LB broth and grown for 6 hours at 200 rpm at 27 degrees. *Agrobacterium* was centrifuged for 10 minutes, and the pellet resuspended at an optical density of 0.2 at 660 nanometers in AB minimal induction media. This was incubated 15 hours at 27 degrees Celsius with shaking (200 rpm). The *Agrobacterium* culture was centrifuged for 10 minutes and the pellet washed with 10 milliliters Lynx 1040 and resuspended in 5 milliliters inoculation medium. The optical density was adjusted to 1.0 and used for inoculation.

Four experiments (designated A, B, C, and D respectively) were performed. Each experiment compared embryos obtained by manual excision to embryos obtained by a method of the present invention: excision by a liquid jet (experiments A, B, and D) or excision by a gas jet (experiment C). The liquid jet in experiments A and B used ordinary tap water and a nozzle made of a pipette tip. Experiment C tested a gas jet using air from a compressed-air pump and a nozzle made of a pipette tip. The liquid jet in experiment D used ½ MSPL medium as the liquid and a solid stream nozzle with an equivalent orifice diameter of 0.020 inches (catalogue number TP000050-SS, Agricultural Division of Spraying Systems Co., Dillburg, Pa.).

Corn ears were harvested twelve days after pollination and sterilized by soaking in a 1-liter bottle of 80% ethanol for 3 minutes. Embryos were manually excised by cutting off the top third of the kernel with a scalpel and removing the embryo from the kernel using a narrow spatula. The collected embryos were excised into 1 milliliter of ½ MSPL medium in a single microcentrifuge (Eppendorf) tube. The medium was removed and replaced with 1 milliliter of *Agrobacterium tumefaciens* prepared as described below Embryos were also substantially isolated using a fluid (liquid or gas) jet, following procedures similar to those described in Examples 10 and 11. The fluid jet was used to excise the remaining embryos on the ears after removing the top third of the kernel with a scalpel. The ear was positioned so that the fluid jet was aimed into individual cut kernels in succession to dislodge both the embryo and non-embryo tissue (endosperm). The kernel contents removed from the ear were passed through a coarse screen to remove large pieces of endosperm, and the embryos were collected on sterile cheesecloth. Embryos were transferred using a small spatula from the cheesecloth into a microcentrifuge tube containing 1 milliliter of ½ MSPL medium. After all of the embryos were collected, ½ MSPL medium was removed and replaced by 1 milliliter of *Agrobacterium tumefaciens* inoculant.

Embryos prepared by the various excision methods were subjected to the same inoculation, selection, and regeneration procedures. Suitable procedures, including descriptions of media and reagents, for transformation of plants using glyphosate selection and GFP as a reporter have been disclosed in United State Patent Application Publication Number 2004/0244075 to Cai et al., which is incorporated by reference in its entirety herein.

Embryos were inoculated with 1.0 milliliters of *Agrobacterium* for 5 minutes. The contents of the microcentrifuge tube were poured onto a plate of co-culture medium, and co-cultured for 18 hours at 23 degrees Celsius. Embryos were transferred next to induction MS medium, and cultured at 30 degrees Celsius for 13 days. Calli derived from the transformation were cultured at 27 degrees Celsius for 11 days prior to regeneration. At this time, GFP positive sectors were counted using a fluorescence microscope. For regeneration, calli derived from each embryo were individually transferred to MS/6 BA medium and cultured in a light room for 7 days, after which each greening callus was transferred to MSOD medium and returned to the light room for 17 additional days. Resulting shoots were transferred to Phytatrays containing regeneration medium (consisting of 2.165 g MS basal salts, 5 milliliters 100×MS vitamins, and 20 grams sucrose made up to 1 liter in water and autoclaved, pH adjusted with KOH to 5.8, solidified by autoclaving with 3 g Phytagel, and with 0.75 milliliters of 1 milligram per milliliter indole-3-butyric acid, 0.5 milliliters of 1 milligram per milliliter 1-naphthaleneacetic acid, and 0.2 milliliters 0.5 molar glyphosate added). After about 3 weeks, transgenic plants were hardened off by transplanting rooted shoots in peat pots containing soil mix and grown at 26 degrees Celsius.

The results of these experiments are summarized in Table 1. The number of embryos that were transformable is estimated from the number of GFP-positive embryos. Overall transformation and regeneration frequency is given as the percentage of GFP-positive plants regenerated from the inoculated embryos. These results demonstrate that various methods and devices of the present invention are useful for providing multiple monocot embryos suitable for genetic transformation or tissue culture.

TABLE 1

| experiment | excision method | number of embryos inoculated | number of GFP-positive embryos | transformation frequency | number of plants to soil | transformation/regeneration frequency |
|---|---|---|---|---|---|---|
| A | manual | 56 | 23 | 41% | 6 | 11% |
|   | liquid jet | 44 | 8 | 18% | 3 | 6.8% |
| B | manual | 22 | 11 | 50% | 6 | 27% |
|   | liquid jet | 23 | 4 | 17% | 1 | 4% |
| C | manual | 33 | 27 | 82% | n/a | n/a |
|   | gas jet | 61 | 19 | 31% | n/a | n/a |
| D | manual | 36 | 17 | 47% | n/a | n/a |
|   | liquid jet | 166 | 51 | 31% | n/a | n/a | n/a: data not available

All of the materials and methods disclosed and claimed herein can be made and used, as instructed by the above disclosure, and without undue experimentation, by a person of ordinary skill in the art. Although the materials and methods of this invention have been described in terms of preferred embodiments and illustrative examples, it will be apparent to those of skill in the art that variations may be applied to the materials and methods described herein without departing from the concept, spirit, and scope of the invention. All such similar substitutes and modifications apparent to those skilled in the art are deemed to be within the concept, spirit, and scope of the invention as further defined by the appended claims.

What is claimed is:

1. A method of providing monocot embryos suitable for transformation or tissue culture, comprising:
   (a) providing multiple monocot seeds containing immature embryos having an opening in the pericarp of said seeds; and
   (b) applying force to said seeds sufficient to extract said immature embryos from said seeds, wherein said extracted immature embryos comprise embryos or pieces of embryos suitable for genetic transformation or tissue culture; wherein said force comprises mechanical positive pressure applied to the exterior of said seeds.

2. The method of claim 1, further comprising separating said extracted immature embryos from associated non-embryo tissue, wherein said separated extracted immature embryos comprise embryos suitable for tissue culture.

3. The method of claim 1, wherein said monocot is in the family Poaceae.

4. The method of claim 1, wherein said monocot is a *Zea* species.

5. The method of claim 4, wherein said multiple monocot seeds comprise multiple corn kernels on at least one corn ear.

6. The method of claim 1, wherein said embryos suitable for tissue culture comprise intact embryos.

7. The method of claim 1, wherein said embryos suitable for tissue culture comprise partial embryos.

8. The method of claim 1, wherein said tissue culture comprises transformation.

9. The method of claim 1, further comprising:
   c) regenerating said extracted immature embryos.

10. The method of claim 9, wherein said regeneration results in callus formation.

11. The method of claim 9, wherein said regeneration results in at least one fertile plant.

12. The method of claim 2, wherein said separating comprises use of at least one of size-exclusion, hydrophobic separation, and density differentials.

\* \* \* \* \*